(12) United States Patent
Tateshima et al.

(10) Patent No.: US 8,487,284 B2
(45) Date of Patent: Jul. 16, 2013

(54) PROHEALING ENDOVASCULAR DEVICES

(75) Inventors: Satoshi Tateshima, Pacific Palisades, CA (US); Takahiro Ogawa, Rolling Hills Estates, CA (US); Fernando Vinuela, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/356,563

(22) Filed: Jan. 23, 2012

(65) Prior Publication Data

US 2012/0205556 A1 Aug. 16, 2012

Related U.S. Application Data

(63) Continuation of application No. PCT/US2010/043152, filed on Jul. 23, 2010.

(51) Int. Cl.
*A61F 2/82* (2006.01)
*A61F 2/90* (2006.01)

(52) U.S. Cl.
USPC ........ 250/504 R; 250/493.1; 604/17; 604/27; 604/28; 604/57; 604/93.01

(58) Field of Classification Search
USPC ................ 250/504 R, 493.1; 604/19, 27, 28, 604/57, 93.01, 94.01
See application file for complete search history.

(56) References Cited

U.S. PATENT DOCUMENTS

| 6,986,868 | B2 * | 1/2006 | Madsen ........................ 422/23 |
| 7,001,410 | B2 * | 2/2006 | Fisher et al. .................. 606/229 |
| 7,166,570 | B2 * | 1/2007 | Hunter et al. ............... 514/21.92 |
| 7,247,387 | B1 * | 7/2007 | Huang .......................... 428/447 |
| 7,785,271 | B2 * | 8/2010 | Fujiwara et al. .............. 600/583 |
| 8,048,437 | B2 * | 11/2011 | Nilsson et al. ................ 424/422 |
| 8,088,145 | B2 * | 1/2012 | Zhu et al. ..................... 606/213 |
| 2004/0158323 | A1 * | 8/2004 | Lisk et al. .................... 623/6.56 |
| 2007/0039884 | A1 * | 2/2007 | Lisk et al. .................... 210/639 |
| 2008/0004691 | A1 | 1/2008 | Weber et al. |
| 2008/0233626 | A1 * | 9/2008 | Li .............................. 435/173.1 |
| 2008/0281410 | A1 | 11/2008 | Maresta et al. |
| 2011/0264057 | A1 * | 10/2011 | Eversull et al. .............. 604/265 |
| 2012/0258313 | A1 * | 10/2012 | Wen et al. .................... 428/412 |
| 2012/0263863 | A1 * | 10/2012 | Nesbitt ....................... 427/2.12 |
| 2012/0271248 | A1 * | 10/2012 | Nesbitt et al. ................ 604/265 |

FOREIGN PATENT DOCUMENTS

KR 10-2009-0074365 7/2009
WO WO 2009/084902 7/2009

* cited by examiner

*Primary Examiner* — David A Vanore
(74) *Attorney, Agent, or Firm* — DLA Piper LLP (US)

(57) ABSTRACT

The present invention provides endovascular devices and the methods of making and using the same. The endovascular device is a prohealing endovascular device that comprises a super hydrophilic surface. The super hydrophilic surface is generated by a method comprising a step of irradiating a surface of the endovascular device with a high energy radiation for a period of time to cause the surface to become super hydrophilic.

21 Claims, 8 Drawing Sheets

PROHEALING ENDOVASCULAR DEVICES

CROSS-REFERENCE TO RELATED APPLICATIONS

This application is a continuation of PCT/US2010/043152, filed on Jul. 23, 2010, which claims the benefit of U.S. provisional application No. 61/228,764 filed Jul. 27, 2009. The teaching in these applications is incorporated hereto in its entirety by reference.

FIELD OF THE INVENTION

The present invention generally relates to the art of endovascular devices and the methods of making and using the same.

BACKGROUND OF THE INVENTION

Current endovascular procedures to treat vascular diseases use a variety of metallic devices, e.g., guidewires, stents, filters, cage-like vascular plugs, and coils. One of the most popular materials used for the endovascular metallic devices is NiTi/Nitinol, so called shape memory alloy. Although endovascular devices made of NiTi demonstrate a great performance in human vessels, there are several intrinsic limitations. Another common metallic material for endovascular device is Cobalt-Chromium alloy (CoCr), which is often used for stents.

First limitation is a friction between a metallic device and catheter. A metallic device is inserted into a plastic catheter, and is pushed out or twisted in the catheter. In order to reduce the friction, the inner lumen of catheter or the surface of some metallic guidewire has a hydrophilic polymer coating. However, such a hydrophilic coating is not enough to overcome this limitation. The hydrophilic polymer coating comes off from the device relatively easily. Also certain devices such as a stent are not easily coated with the hydrophilic polymers. In fact, most stents are not coated with hydrophilic materials. The friction makes the delivery of stent or coil into a target lesion difficult and unsafe. Furthermore, the friction makes it difficult to design a longer stent because a longer stent would induce an increase in friction so as to be difficult to deliver to a target lesion. The friction also makes it difficult to control (twist and push/pull) a metallic guidewire.

The second limitation is that a patient who receives an intra-arterial metallic device placement, particularly a metallic stent placement, is required to be medicated with antiplatelet medications such as Aspirin or Plavix, so called blood thinners, for several months in order to prevent clotting and occlusion of stent lumen. The blood thinners itself carry a risk of spontaneous bleeding in organs such as brain and gastrointestinal tract. Even with the blood thinning medications, the clotting of important arteries occurs not infrequently after the placement of metallic devices in the vessels since the devices are a foreign material for the human vessels. Although the clotting due to the intravascular metallic device placement involves a complex multi-factorial processes, inflammatory reaction and vascular injury are important factors that activate the coagulation cascade. Furthermore, the metallic device should be covered with native tissues and cells in the healing process so that the foreign material does not have a direct exposure to blood flow.

Therefore, there is a need for an endovascular device having an enhanced rate of endothelialization and/or neointima coverage as well as an enhanced affinity of the device with a native vascular tissue. An enhanced rate of endothelialization and/or neointima coverage would allow sooner cessation of blood-thinning medications so as to reduce or minimize the risk of spontaneous bleeding in organs such as brain and gastrointestinal tract.

The embodiments described below address the above identified problems and needs.

SUMMARY OF THE INVENTION

According to embodiments of the present invention, it is provided a prohealing endovascular device, comprising a surface generated by a method comprising irradiating a surface of the endovascular device with a high energy radiation for a period of time to cause the surface to become a super hydrophilic surface.

The high energy radiation can be any high energy radiation. In some embodiments, the high energy radiation is ultraviolet.

The endovascular device can comprise a metallic and/or non metallic material. In some embodiments, the metal can be any of gold, titanium, platinum, tantalum, niobium, nickel, iron, chromium, cobalt, zirconium, magnesium, magnesium, aluminum, palladium, Nitinol, cobalt-chromium alloy, an alloy formed thereof, or combinations thereof.

The endovascular device of invention has a variety of advantageous properties. In some embodiments, it has an increased rate of endothelialization as compared with an endovascular device without treatment by irradiation, for example, increased by 10%. In some embodiments, the endovascular device of invention has an increased rate of neointima coverage as compared with an endovascular device without treatment by irradiation, for example, increased by 10%. In some embodiments, the endovascular device of invention has an increased affinity of the device with a native vascular tissue as compared with an endovascular device without treatment by irradiation, for example, increased by 10%. In some embodiments, the endovascular device of invention has a reduced friction during the insertion or delivery of the endovascular device, for example, reduced by 10%. In some embodiments, the endovascular device of invention has a decreased level of inflammation at a site receiving the endovascular device of invention as compared with an endovascular device without treatment by irradiation, for example, decreased by 10%.

In some embodiments, in combination with any or all of the various embodiments above, the endovascular device can have a surface treated by surface-treating the endovascular device prior to irradiating the surface of the endovascular device.

The endovascular device can be any endovascular device in medicine or veterinary medicine. In some embodiments, the endovascular device is selected from stents, grafts, stent-grafts, catheters, leads and electrodes, clips, shunts, closure devices, valves, guidewires, filters, cage-like vascular plug, coils, and particles.

In some further embodiments of the present invention, it is provided a method of treating or ameliorating a disorder involving a vascular condition, comprising implanting in a subject the endovascular device of the various embodiments disclosed herein. The disorder can be, e.g., one of atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, urethral obstruction and tumor obstruction.

In some further embodiments of the present invention, it is provided a method of generating an endovascular device according to the various embodiments disclosed herein, the method comprising:

irradiating a surface of the endovascular device with a high energy radiation for a period of time to cause the surface to become a super hydrophilic surface, thereby generating the endovascular device.

The period can be, e.g., about 10 minutes or longer, or about 60 minutes or longer.

In some embodiments, the method further comprises surface-treating the endovascular device prior to irradiating the surface of the endovascular device. Such surface-treating can be, e.g., treating the endovascular device by acid-etching, sand-blasting, or machining.

DETAILED DESCRIPTION OF THE INVENTION

According to embodiments of the present invention, it is provided a method of generating a prohealing endovascular device, comprising irradiating a surface of the endovascular device with a high energy radiation for a period of time to cause the surface to become a hydrophilic or super hydrophilic surface, generating a prohealing endovascular device having an enhanced rate of endothelialization. The endovascular devices have a hydrophilic or super hydrophilic surface as opposed to endovascular devices hydrophobic nature without this treatment.

As used herein, irradiating a surface of the endovascular device with a high energy radiation for a period of time to cause the surface to become a hydrophilic or super hydrophilic surface is also referred to as hydrophilic conversion or super hydrophilic conversion of the surface. Such hydrophilic conversion or super hydrophilic conversion of surface (e.g., a titanium surface, NiTi surface, or CoCr surface) imparts important technical features or advantages to an endovascular device subjected to such hydrophilic conversion or super hydrophilic conversion as opposed to an endovascular device that is not subjected to treatment according to the method disclosed herein. For example, such hydrophilic conversion or super hydrophilic conversion of surface increases the affinity of a device with a vascular tissue, which accelerates the healing process and reduces the clotting problem. In addition, an enhanced affinity of the device with native vascular tissue should decrease the level of such an adverse inflammatory reaction after the device placement. As opposed to an endovascular device that is not subjected to treatment according to the method disclosed herein, an important advantage of the hydrophilic conversion or super hydrophilic conversion of surface of an endovascular device is an enhanced rate of endothelialization and/or neointima coverage as well as an enhanced affinity of the device with a native vascular tissue; an enhanced rate of endothelialization and/or neointima coverage would allow sooner cessation of blood-thinning medications so as to reduce or minimize the risk of spontaneous bleeding in organs such as brain and gastrointestinal tract.

Additionally, the hydrophilic conversion or super hydrophilic conversion of surface (e.g., a titanium surface, a NiTi surface or a CoCr surface) also reduces the friction during the insertion or delivery of endovascular metallic devices.

As used herein, the term "enhanced rate of endothelialization and/or neointima coverage" refers to an increase of rate of endothelialization and/or neointima coverage of about 1% or higher, about 5% or higher, about 10% or higher, about 20% or higher, about 50% or higher, about 75% or higher, about 100% or higher, about 200% or higher, about 500% or higher, or about 1000% or higher at a given time after deployment of an endovascular device described herein. Such a given time can be, e.g., days, weeks, months, or years after deployment of an endovascular device described herein, e.g., about 10 days, about 20 days, about 30 days, about 45 days, about 60 days, about 120 days, about 150 days, about 180 days, about 210 days, about 240 days, about 270 days, about 300 days, about 330 days, about 12 months, about 18 months, about 24 months, about 36 months, about 4 years, about 5 years, or about 10 years.

As used herein, the term "increased affinity" refers to an endovascular device having an affinity of the device with a native vascular tissue increased by at least 1% or higher, by at least 5% or higher, by at least 10% or higher, by at least 20% or higher, by at least 50% or higher, by at least 75% or higher, by at least 100% or higher, by at least 150% or higher, by at least 200% or higher, by at least 400% or higher, by at least 500% or higher, by at least 1000% or higher, by a factor of 50, 100, 1000, or 10000 times or higher.

As used herein, the term "reduced friction" refers to an endovascular device of invention having a surface generated by the method disclosed herein, as compared with an endovascular device without such a treatment, having a friction during the insertion or delivery of the endovascular device reduced by, for example, at least 10%, at least 20%, at least 30%, at least 40%, at least 50%, at least 60%, at least 70%, at least 80%, at least 90%, at least 95%, at least 99%, or about 100%.

As used herein, the term "reduced level of inflammation response" refers to an endovascular device having a surface generated by the method disclosed herein, as compared with an endovascular device without such a treatment, having a level of inflammation response at a site receiving the endovascular device reduced by, for example, at least 10%, at least 20%, at least 30%, at least 40%, at least 50%, at least 60%, at least 70%, at least 80%, at least 90%, at least 95%, at least 99%, or about 100%.

The endovascular device can comprise metallic or non-metallic material. In some embodiments, the material comprises titanium, a Nitinol alloy and/or a cobalt/chromium alloy. In some embodiments, the metallic material can be one of gold, titanium, platinum, tantalum, niobium, nickel, iron, chromium, cobalt, zirconium, magnesium, magnesium, aluminum, palladium, an alloy formed thereof, or combinations thereof.

In some embodiments, the method comprising irradiating the surface of an endovascular device with a high energy source, which can be, for example, ultraviolet light, X rays and gamma rays. In some embodiments, the high energy radiation is ultraviolet. The period of time of irradiation can be about 10 minutes or longer, about 30 minutes or longer, about 60 minutes or longer, about 120 minutes or longer, about 6 hours or longer, 12 hours or longer, about 24 hours or longer, or about 48 hours or longer.

In some embodiments, upon deployment, the prohealing endovascular device has a rate of endothelialization increased by at least 1% or higher, by at least 10% or higher, by at least 50% or higher, by at least 100% or higher, or by at least 200% or higher.

In some embodiments, optionally in combination with the aforementioned increased rate of endothelialization, the prohealing endovascular device has an increased rate neointima coverage increased by at least 1% or higher, by at least 10% or higher, by at least 50% or higher, by at least 100% or higher, or by at least 200% or higher.

In some embodiments, optionally in combination with the aforementioned increased rate of endothelialization and/or increased rate of neointima coverage, the prohealing endovascular device has an affinity of the device with a native vascular tissue increased by at least 1% or higher, by at least 10% or higher, by at least 50% or higher, by at least 100% or higher, or by at least 200% or higher.

In some embodiments, the endovascular device of invention has a reduced friction during the insertion or delivery of the endovascular device reduced by, for example, at least 10%, at least 20%, at least 30%, at least 40%, at least 50%, at least 60%, at least 70%, at least 80%, at least 90%, at least 95%, at least 99%, or about 100%.

In some embodiments, the endovascular device of invention has a decreased level of inflammation at a site receiving the endovascular device of invention as compared with an endovascular device without treatment by irradiation reduced by, for example, at least 10%, at least 20%, at least 30%, at least 40%, at least 50%, at least 60%, at least 70%, at least 80%, at least 90%, at least 95%, at least 99%, or about 100%.

In some embodiments, the various embodiments described above can further comprise surface-treating the endovascular device prior to irradiating the surface of the endovascular device. Such surface-treating can be, e.g., acid-etching, sand-blasting, or machining.

In according to embodiments of the present invention, it is provided a prohealing endovascular device. In some embodiments, the prohealing endovascular device is generated according to the various above embodiments of methods. The prohealing endovascular device can be, for example, stents, grafts, stent-grafts, catheters, leads and electrodes, clips, shunts, closure devices, valves, and particles.

In according to further embodiments of the present invention, it is provided a method of treating or ameliorating a disorder involving a vascular condition, the method comprises implanting in a subject the prohealing endovascular device of the various above embodiments. In some embodiments, the disorder is selected from the group consisting of atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, urethral obstruction and tumor obstruction.

As used herein, the term hydrophilic surface refers to a surface having a water wet angle of about 0 to about 60 degrees or lower, e.g., 40 degrees, or 30 degrees. A super hydrophilic surface refers to a surface having a water wet angle of about 0 to 20 degrees or lower, e.g., about 15 degrees, about 10 degrees, or about 5 degrees.

As used herein, the term prohealing refers to attribute of an endovascular device capable of accelerated healing without the use of a drug or agent other than the endovascular device. In some embodiments, a prohealing endovascular device described herein has a hydrophilic or super hydrophilic surface.

Endovascular Devices

The endovascular devices described herein include any endovascular devices currently available in medicine or to be introduced in the future. The devices can be metallic or non-metallic devices. Non-metallic implants include, for example, ceramic devices, calcium phosphate or polymeric devices. Useful polymeric implants are biodegradable or biodurable polymeric devices. Representative ceramic devices include, e.g., bioglass and silicon dioxide devices. Calcium phosphate devices include, e.g., hydroxyapatite, tricalciumphosphate (TCP) devices. Useful polymeric devices include, e.g., poly-lactic-co-glycolic acid (PLGA) and poly-lactic acid (PLA) devices.

Metallic endovascular devices can comprise any biocompatible metallic material. In some embodiments, such biocompatible metallic material includes, for example, titanium, titanium, platinum, tantalum, niobium, nickel, iron, chromium, cobalt, zirconium, magnesium, magnesium, aluminum, palladium, an alloy formed thereof, e.g., stainless steel, and combinations thereof In some embodiments, the metallic material is NiTi (Nitinol) alloy.

The endovascular devices described herein can be porous or non-porous devices. Porous devices generally have better tissue integration while non-porous devices have better mechanical strength.

In some embodiments, the endovascular device used in the method is selected from stents, grafts, stent-grafts, catheters, leads and electrodes, clips, shunts, closure devices, valves, guidewires, filters, cage-like vascular plug, coils, and particles. In some embodiments, the device is a metallic stent.

High Energy Radiation

The endovascular devices with enhanced tissue integration capabilities provided herein can be formed by treating the endovascular devices with a high energy radiation for a period of time. The length of the radiation period depends on the type of implants. For a metallic implant (e.g., a titanium implant), the period of radiation generally ranges from about 1 minute to about 1 month, e.g., from about 1 minute to about 1 hour, from about 1 hour to about 5 hours, from about 5 hours to about 24 hours, from about 1 day to about 5 days, from about 5 days to about 10 days, or from about 10 days to about 1 month. For non-metallic implants, e.g., a biocompatible, biodurable polymeric implant, the period of radiation generally ranges about 1 minute to about 1 month, e.g., from about 1 minute to about 1 hour, from about 1 hour to about 5 hours, from about 5 hours to about 24 hours, from about 1 day to about 5 days, from about 5 days to about 10 days, or from about 10 days to about 1 month.

The term "high energy radiation" includes radiation by light or a magnetic wave. In some embodiments, the term "high energy" refers to a radiation having a wavelength at or below about 400 nm, e.g., about 350 nm, about 300 nm, about 250 nm, about 200 nm, about 150 nm, about 100 nm, about 50 nm, or about 10 nm.

In some embodiments, the radiation can have a wavelength at or below about 5 nm, about 1 nm, about 0.5 nm, about 0.1 nm, about 0.05, about 0.01, about 0.005 or about 0.001 nm. The radiation having a wavelength from about 400 nm to 10 nm is generally referred to as ultraviolet light (UV), the radiation having a wavelength from about 10 nm to 0.1 nm is generally referred to as x-rays, and the radiation having a wavelength from about 0.1 nm to about 0.001 nm is generally referred to as gamma-rays.

The endovascular devices can be radiated with or without sterilization. To one of ordinary skill in the art, the endovascular devices can be sterilized during the process of high energy radiation (e.g., UV radiation).

In anther aspect of the present invention, it is provided a facility or device for radiating endovascular devices. In one embodiment, the facility or device includes a chamber for placing endovascular devices, a source of high energy radiation and a switch to switch on or turn off the radiation. The facility or device may further include a timer. In some embodiments, the facility or device can further include a mechanism to cause the endovascular devices or the high energy radiation source to turn or spin for full radiation of the implants. Alternatively, the chamber for placing endovascular devices can have a reflective surface so that the radiation can be directed to the endovascular devices from different angles, e.g., 360° angle. In some embodiments, the facility or device may include a preservation mechanism of the enhanced bone-integration capability, e.g., multiple irradiation of light, radiolucent implant packaging, packing and shipping.

Method of Treating or Preventing Disorders

An endovascular device according to the present invention can be used to treat, prevent or diagnose various conditions or disorders. Examples of such conditions or disorders include, but are not limited to, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, urethral obstruction and tumor obstruction. A portion of the endovascular device or the whole device itself can be formed of the material, as described herein. For example, the material can be a coating disposed over at least a portion of the device.

In certain embodiments, optionally in combination with one or more other embodiments described herein, the inventive method treats, prevents or diagnoses a condition or disorder selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, urethral obstruction and tumor obstruction. In a particular embodiment, the condition or disorder is atherosclerosis, thrombosis, restenosis or vulnerable plaque.

In certain embodiments, optionally in combination with one or more other embodiments described herein, the endovascular device used in the method is selected from stents, grafts, stent-grafts, catheters, leads and electrodes, clips, shunts, closure devices, valves, and particles. In a specific embodiment, the endovascular device is a stent.

EXAMPLES

Example 1

Studies on Properties of Nitinol Device Treated by Ultra-Violet Irradiation: Enhanced Affinity to Vascular Tissue and Endothelialization and Reduced Inflammation Response Introduction Current minimally invasive interventional procedures for the treatment of vascular diseases use a variety of metallic implant devices such as a stent. The implantation of metallic stents following percutaneous transluminal angioplasty has been widely accepted as an alternative therapy to bypass surgery in cardiovascular, peripheral vascular, and neurovascular interventions. Although endovascular metallic stent implants demonstrate a great performance in human vessels, there are some intrinsic limitations.

First limitation is a friction between a metallic device and catheter. Usually a metallic implant is inserted into a plastic catheter, and is pushed or twisted out of the catheter. The longer or more complex a metallic device becomes, the more friction a treating physician experiences during the delivery. The friction makes the delivery of stent or coil the into a target lesion difficult and unsafe.

The second limitation is that some of the endovascular metallic implants are biologically inactive, which delays the healing process of the vessel that endovascular metallic devices are implanted. The metallic device should be covered with native tissues and cells in the healing process so that the foreign material does not have a direct exposure to blood flow. Furthermore, delayed healing potentially causes unfavorable event such as a stent migration.

The last limitation is that a patient who receives an intra-arterial metallic device placement, particularly a metallic stent placement, is required to be medicated with anti-platelet medications such as Aspirin or clopidogrel, so called blood thinners in order to prevent unfavorable excessive clotting. The blood thinning medications carry a risk of spontaneous bleeding in organs such as brain and gastrointestinal tract. Even with the blood thinning medications, the clotting of important arteries occurs not infrequently after the placement of metallic devices in the vessels since the devices are a foreign material for the human vessels. The metallic device should be covered with native tissues and cells in the healing process so that the foreign material does not have a direct exposure to blood flow.

We describe a method that potentially overcomes the above-mentioned limitations of endovascular devices made of NiTi. We found that ultraviolet (UV) light treated NiTi sheet, wire, and stent have been demonstrated to show super-hydrophilic nature as opposed to hydrophobic nature without this treatment. This super-hydrophilic conversion of NiTi surface may increase the affinity of a metallic device and vascular tissue, which may accelerates the healing process after the implantation of metallic devices. In this study, we evaluated the application of UV irradiation to NiTi metal surface, and the difference in vitro bioactivity with and without UV irradiation.

Materials and Methods

Ultraviolet (UV) Light Treatment

NiTi sheet samples (20×20 mm) were treated with UV for 48 hours under ambient conditions using a 15 W bactericidal lamp (Toshiba, Tokyo, Japan); intensity; ca. 0.1 mW/cm$^2$ (1=360±20 nm) and 2 mW/cm$^2$ (1=250±20 nm). Surface energy of each NiTi sheet surface was evaluated by the contact angle of 1 ml $H_2O$ using an automatic contact angle-measuring device (DCA-VZ, Kyowa Interface Science, Saitama, Japan).

Measurement of Protein Adsorption

Bovine serum albumin, fraction V (Pierce Biotechnology, Inc., Rockford, Ill.) was used as a model protein. Three hundred ml of protein solution (1 mg/ml protein/saline) was spread over a NiTi sheet surface using a pipette. After 24 hour of incubation in a sterile humidified condition at 37° C., non-adherent protein removed and washed twice using saline with 0.9% sodium chloride. Two hundred ml aliquots of the initial and removed solutions were mixed with 200 ml microbicinchoninic acid (Pierce Biotechnology, Inc., Rockford, Ill.) and incubated at 37° C. for 60 minutes. The amount of protein was quantified by a microplate reader at 562 nm.

Human Endothelial Cell Culture

Human aortic endothelial cells (HAOEC, Cell Applications, Inc. San Diego, Calif.) were cultured in Endothelial Cell Growth medium. Cells were incubated in a humidified atmosphere of 95% air, 5% $CO_2$ at 37° C. At 80% confluency of the last passage, cells were detached using 0.25% trypsin-1 mM EDTA-4Na and seeded onto NiTi surfaces with and without UV treatment at a density of 3×10$^4$ cells/cm$^2$. The culture medium was renewed every three days.

Migration Assay

Migration of endothelial cells to NiTi surfaces was examined using dual-chamber migration assay (345-024K, Trevigen, Gaithersburg, Md.). The endothelial cells were seeded into the top chamber in the culture medium. A NiTi sample with or without UV treatment was placed at the bottom of the lower chamber. The percentage of the cell penetrated into the lower chamber after 2 hours of incubation at 37° C., through polyester membrane with 8-mm diameter pores, was analyzed by a plate reader after calcein AM stain.

Cell Attachment and Metabolic Activity Assays

Initial attachment of cells was evaluated by measuring the quantity of the cells attached to NiTi substrates after 6 hours and 24 hours of incubation. The cells were gently rinsed twice with PBS and treated with 0.1% collagenase in 300 ml of 0.25% trypsin-1 mM EDTA-4Na for 15 min at 37° C. A hematocytometer was used to count the number of detached cells obtained. SEM was taken to confirm the absence of any cell remnant on the substrates. Cellular metabolic activity was evaluated by WST-1 based colorimetry (WST-1, Roche Applied Science, Mannnheim, Germany) after 24 hour of incubation. The culture well was incubated at 37° C. for 4 hours with 100 ml tetrazolium salt (WST-1) reagent. The amount of formazan product was measured using an ELISA reader at 420 nm.

Cell Morphology

After 3 hour of culture endothelial cells were fixed in 10% formalin, and stained using fluorescent dyes, DAPI (nuclei green color, Vector, Calif.) and rhodamine phalloidin (actin filament red color, Molecular Probes, OR). Confocal laser scanning microscopy was used to examine cell morphology and cytoskeletal arrangement.

Cell Proliferative Activity

Propagated cells were quantified as cell density at culture days of 2 and 4. Cells were gently rinsed twice with PBS and treated with 0.1% collagenase in 300 μl of 0.25% trypsin-1 mM EDTA-4Na for 5 minutes at 37° C. A hematocytometer was used to count the number of detached cells. SEM was used for the selected culture to confirm the absence of any cell remnant on the substrates. The proliferative activity of the cells was also measured by BrdU incorporation during DNA synthesis. At day 2 of culture, 100 ml of 100 mM BrdU solution (Roche Applied Science, Mannheim, Germany) was added to the culture wells and incubated for 10 hours. After trypsinizing the cells and denaturing the DNAs, the cultures were incubated with anti-BrdU conjugated with peroxidase for 90 minutes and reacted with tetramethylbenzidine for color development. Absorbance at 370 nm was measured using an ELISA reader.

Statistical Analysis

All of the experiments described above were performed in triplicates. Differences between untreated control NiTi and UV-treated NiTi cultures were examined via t-test; $p<0.05$ was used as a level of statistical significance.

Results

Conversion of NiTi by UV from Hydrophobic to Hydrophilic Status

Figure 1:
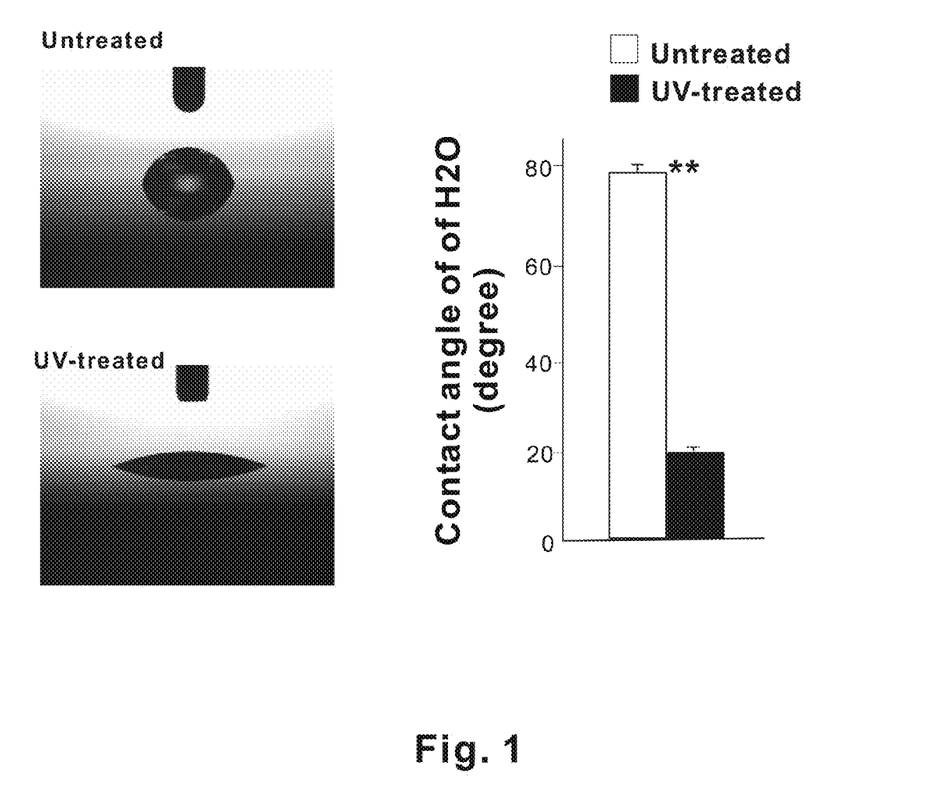
FIG. 1 shows the hydrophilic status of NiTi surface with or without ultraviolet (UV) treatment. Photographic images of 1 ml $H_2O$ droplets pipetted onto NiTi surfaces (left panels). Mean±SD contact angle of $H_2O$ on the NiTi surfaces (Bar graph). n=3. **Significantly different from the fresh surface, p<0.01.

The contact angle of $H_2O$ which was approximately 80° on untreated control NiTi surfaces became lower than 20° after the treatment of UV light, indicating the conversion of hydrophobic surface to hydrophilic surface (FIG. 1). Images of the $H_2O$ droplet showed an increased area of water spread on UV-treated NiTi surfaces (left panels in FIG. 1).

Increased Protein Adsorption Capacity on UV-treated NiTi

Figure 2:
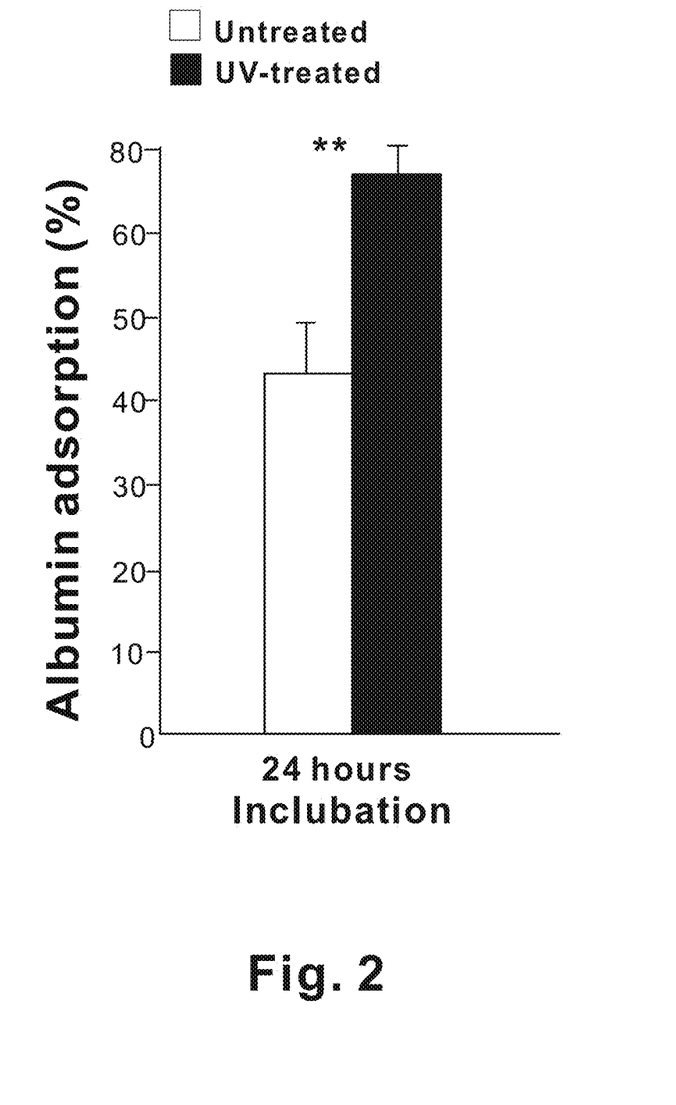
FIG. 2 shows the mean±SD adsorption rate of bovine serum albumin after 24 hours of incubation on NiTi surfaces with or without UV treatment. n=3. **Significantly different from the fresh surface, p<0.01.

FIG. 2 shows the amount of albumin adsorbed to NiTi surface during 24 hour incubation. There was a significant increase in the adherent albumin over UV treated hydrophilic surface than over untreated surface.

Increased Cell Attractiveness of UV-treated NiTi

Figure 3:
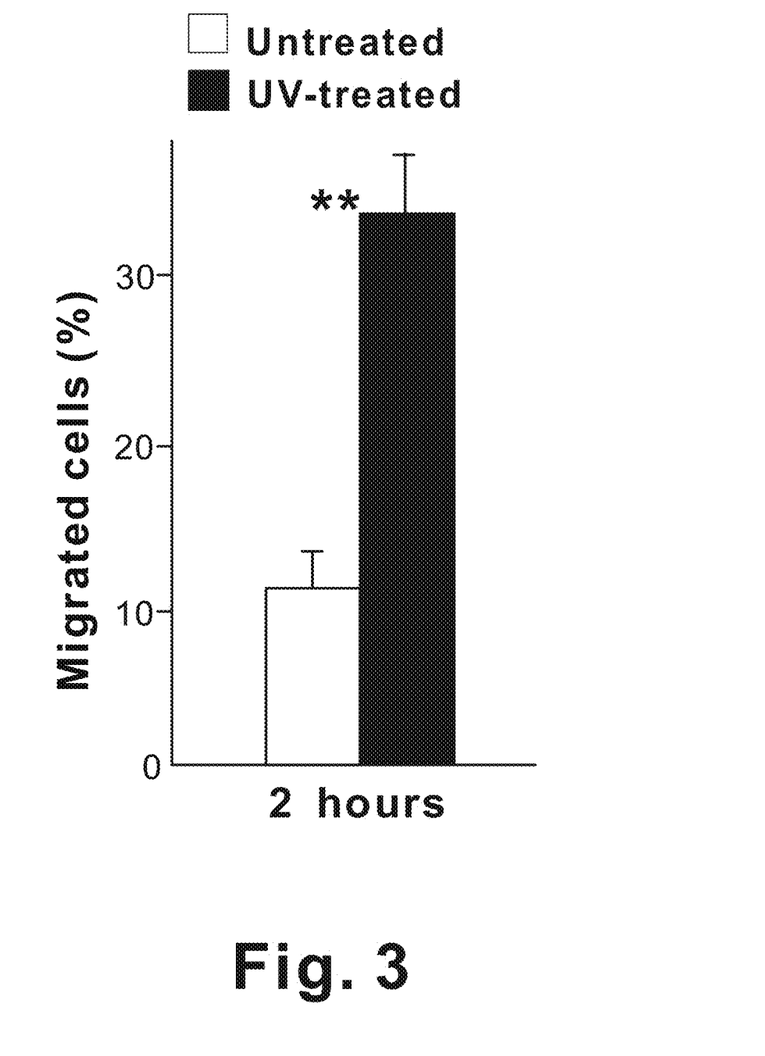
FIG. 3 shows the mean±SD number of migrated endothelial cells onto NiTi surfaces after 2 hours of incubation. n=3. **Significantly different from the fresh surface, p<0.01.
Figure 4:
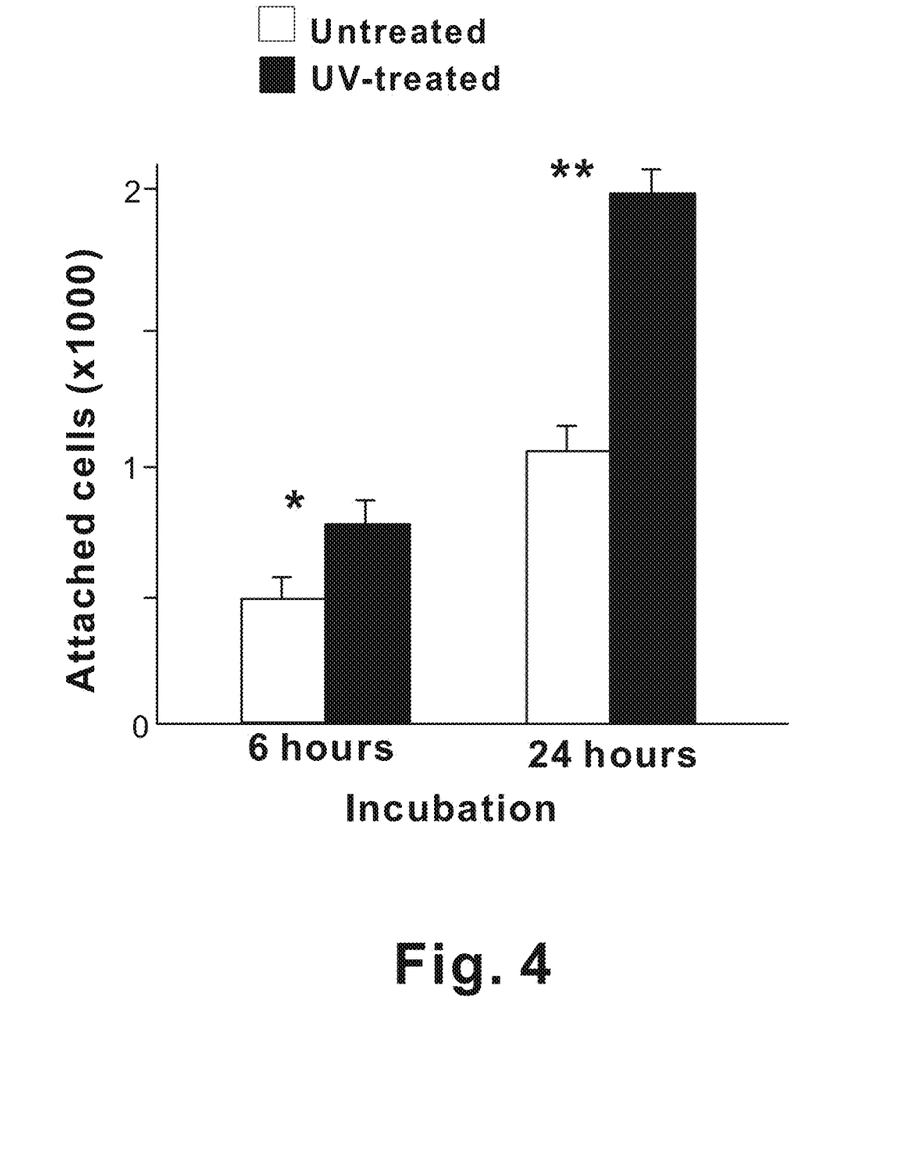
FIG. 4 shows the mean±SD number of attached endothelial cells to NiTi surfaces after 6 and 24 hours of incubation. n=3. **Significantly different from the fresh surface, p<0.01. *Significantly different from the fresh surface, p<0.05.
Figure 5:
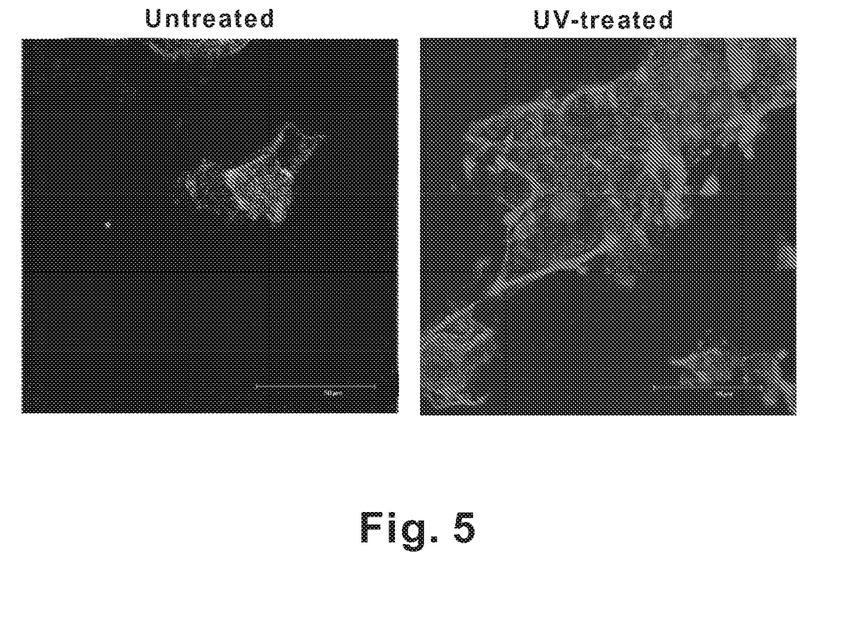
FIG. 5 shows the initial spread and cytoskeletal arrangement of human endothelial cells 2 hour after seeding onto untreated and UV-treated NiTi surfaces. Representative confocal microscopic images of endothelial cells with dual staining of DAPI for nuclei (green) and rhodamine phalloidin for actin filaments (red) are shown.

The number of aorta-derived endothelial cells migrated during 2 hours was over 2.5 times greater on UV-treated NiTi than on untreated NiTi (FIG. 3). Likewise, the number of the cells attached during 6 hours and 24 hours of incubation was significantly increased on UV-treated NiTi (FIG. 4). The number was doubled after 24 hours of incubation. Confocal images with the nuclear and cytoskeletal stains revealed that endothelial cells spread more on UV-treated NiTi and the cytoskeletal development was expedited compared with those on untreated NiTi (FIG. 5).

Increased Bioactivity of UV-treated NiTi

Figure 6:
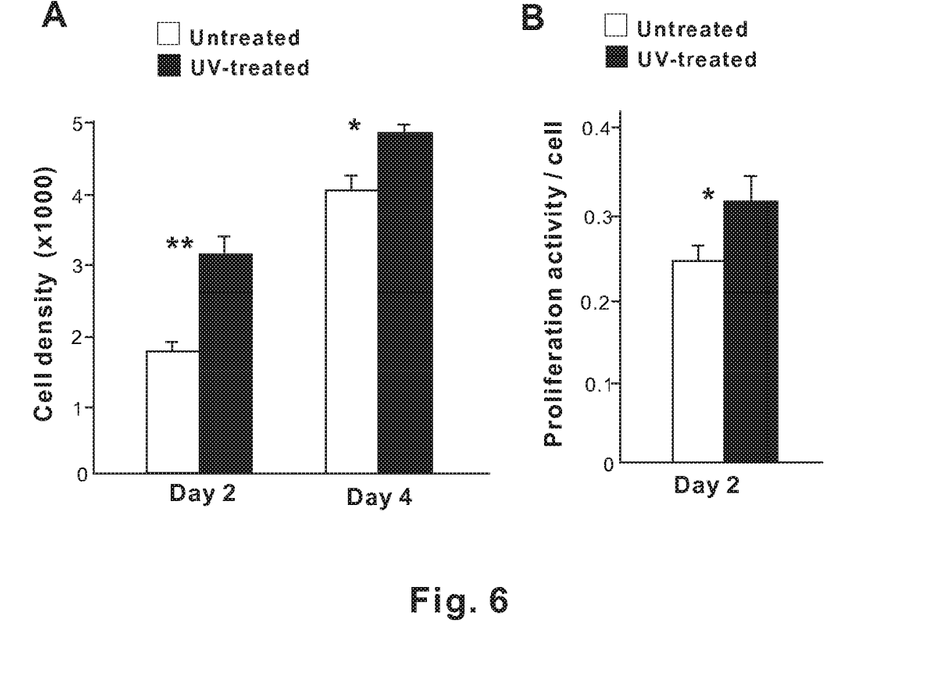
FIGS. 6A and 6B shows the mean±SD number (A) and BrdU DNA incorporation (B) of endothelial cells on NiTi surfaces after 2 and 4 days of culture. n=3. **Significantly different from the fresh surface, p<0.01. *Significantly different from the fresh surface, p<0.05.
Figure 7:
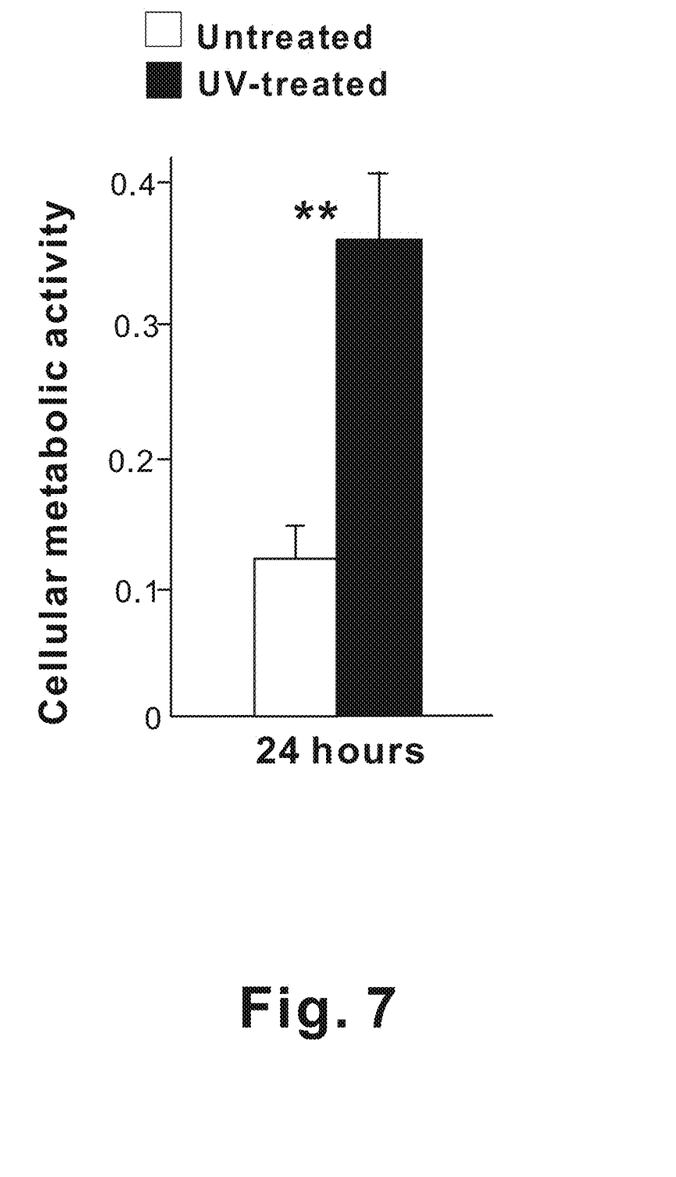
FIG. 7 shows the mean±SD cellular metabolic activity of endothelial cells, measured by WST-1 stain, on NiTi surfaces after 24 hour of culture. n=3. **Significantly different from the fresh surface, p<0.01.

The number of endothelial cells at days 2 and 4 of culture was significantly greater on UV-treated NiTi than on untreated NiTi surfaces (FIG. 6A). Proliferation activity of the cells was also increased on UV-treated NiTi (FIG. 6B). Metabolic activity of the cells measured 24 hours after seeding was approximately 2.5 greater on UV-treated NiTi than on untreated NiTi (FIG. 7).

Decreased Level of Inflammatory Response

Figure 8:
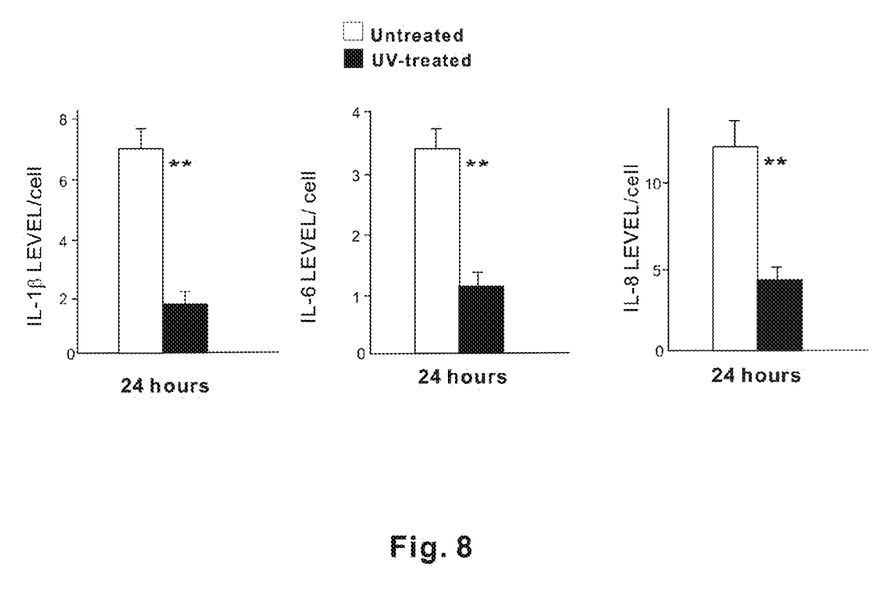
FIG. 8 shows NiTi surfaces treated by UV-irradiation elicit decreased level of inflammation response.

FIG. 8 shows the UV treated group elicits a markedly and substantially lower of inflammation as evidenced by the markedly and substantially lower IL1beta, IL6, IL8 levels elicited by the UV treated group. What is significant about lower ILs with UV group is that UV treatment elicits less inflammatory reactions.

Discussion

To our knowledge, this is the first study which demonstrated UV irradiation to NiTi induces the conversion of hydrophobic to hydrophilic surface of NiTi. The result of this study showed that the contact angle of a water drop over the UV irradiate surface of NiTi sheet was approximately 20 degrees, which we may call a supper-hydrophilic conversion. Currently the inner lumen of delivery endovascular catheter or the surface of some metallic devices has a hydrophilic polymer coating in order to reduce the friction during the delivery. However such a hydrophilic polymer coating comes off from the device relatively easily. Moreover, certain devices such as a stent are not easily coated with the hydrophilic polymers. In fact, most of metallic stents are not coated with hydrophilic materials. The advantage of the hydrophilic conversion of NiTi surface by UV irradiation is that it does not come off easily unlike current polymer hydrophilic coating on endovascular metallic devices. UV irradiation to the surface of a complex-shaped metallic implants such as stents theoretically does not change their mechanical characteristics. The hydrophilic conversion of NiTi may reduce the friction between a complex-shape metallic device and catheter, and may make the delivery of the metallic device more controllable and safer in clinical setting.

The hydrophilic conversion of NiTi surface may bring favorable characteristics for the use of endovascular implant. The adsorption of proteins in the surrounding bio-fluid onto a metallic implant surface is the first important step of our body response to the implant, since the adsorbed protein mediates the cellular response to the implant. Albumin is the most common plasma protein in the blood. Our data demonstrated that the amount of albumin adsorption significantly increased over the UV treated NiTi surface when compared to the untreated surface. This proposes that the hydrophilic conversion of NiTi metallic implants after UV irradiation may accelerates the healing process of the vessel where the implant was placed.

Likewise, hydrophilic conversion may reduce the chance of unfavorable excessive thrombus formation within the metallic implant in vivo, since a layer of albumin minimizes the aggregation of platelets. Our results showed an increase in bioactivity, maturity, and proliferation of endothelial cells over the UV treated NiTi surface. UV treated NiTi sheets were covered with endothelial cells faster than without UV treatment. The faster coverage of metallic implants by endothelial cells works positively on reducing the chance of unfavorable thrombus formation. Also the faster endothelial coverage and accelerated healing potentially makes earlier cessation of anti-platelet medications possible, thus reducing the risk of bleeding complication associated with those medications. The faster endothelial coverage and accelerated healing after the placement of endovascular metallic implants also reduced the chance of late device migration.

It is remarkable that the devices treated by UV-irradiation elicit markedly and substantially lower inflammation responses. Less inflammation in the tissue post-implantation indicates faster would healing, faster endothelial/neointimal coverage over UV treated device, lower incidence of unfavorable thrombosis or in-situ clot formation over the metal implant surface, which are key considerations in the intervention technologies such as stenting, etc.

Conclusion

UV irradiation to NiTi induced hydrophilic conversion of the surface. The increase in albumin adsorption, endothelial cell attractiveness, and bioactivities of endothelial cells indicates that the biocompatibility of the endovascular metallic device made of NiTi is enhanced by the UV irradiation. Our in vitro data suggests that the affinity of NiTi with vascular tissue increases after the UV irradiation.

Example 2

Studies on Hydrophilic Modification of Cobalt-Chromium Surfaces

Materials and Methods

Ultraviolet (UV) Light Treatment

Sandblasted and machined Cobalt-Chromium samples were treated with UV for 48 h under ambient conditions using a 15 W bactericidal lamp (Toshiba, Tokyo, Japan); intensity; ca. 0.1 mW/cm$^2$ ($1=360\pm20$ nm) and 2 mW/cm$^2$ ($1=250\pm20$ nm). Surface energy of each of the surfaces was evaluated by the contact angle of 1 ml H$_2$O using an automatic contact angle measuring device (DCA-VZ, Kyowa Interface Science, Saitama, Japan).

Results

Conversion of Cobalt-Chromium by UV from Hydrophobic to Hydrophilic Status

Figure 9:
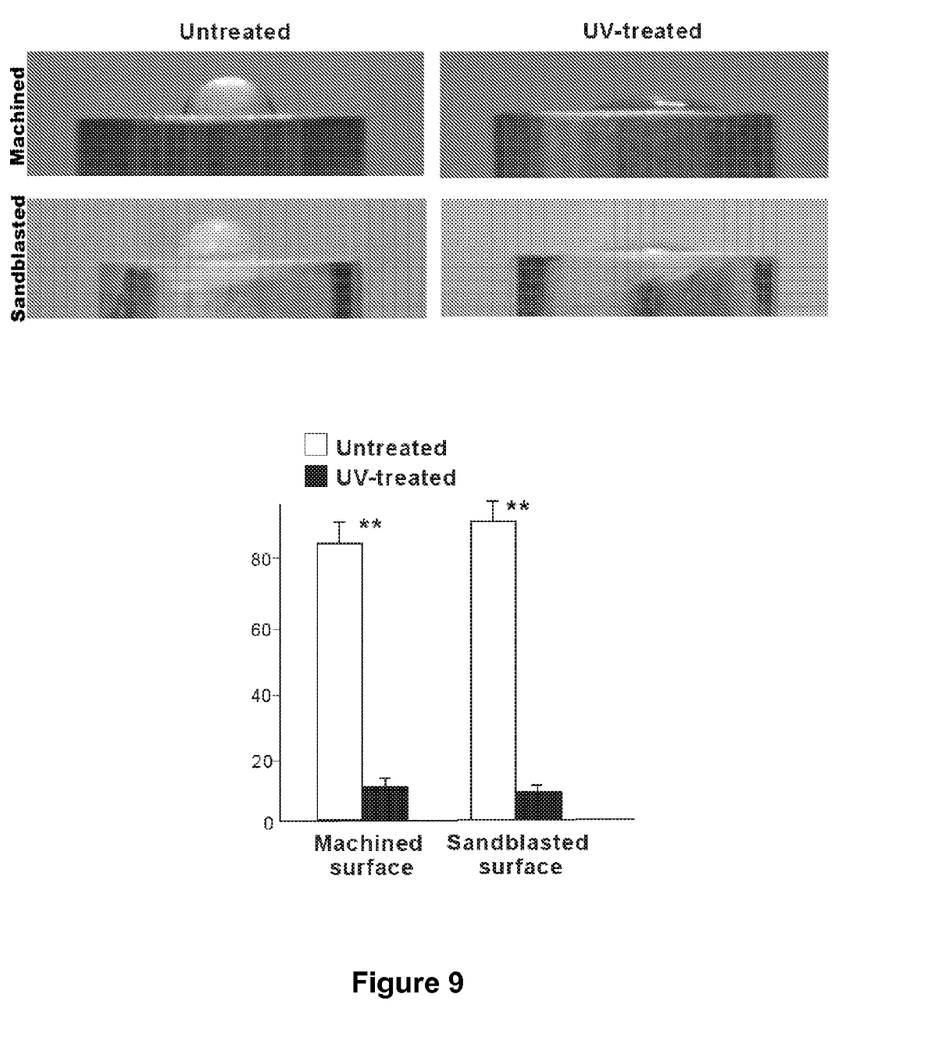
FIG. 9 shows an alteration in the contract angle of Cobalt-Chromium alloy/CoCr surface with or without UV treatment. Photographic images (side views) of 1 ml of $H_2O$ droplets pipetted onto sandblasted and machined CoCr surfaces with or without UV treatment. **Significantly different from the fresh surface, p<0.01

The contact angle of H$_2$O which was approximately 80-90° on untreated control Cobalt-Chromium surfaces became lower than 20° after the treatment of ultraviolet (UV) light, indicating the conversion of hydrophobic surface to hydrophilic surface (FIG. 9).

Summary

The above data clearly show that UV irradiation to NiTi and Cobalt-Chromium, two most common metallic materials used in stents, induces the conversion of hydrophobic to hydrophilic surface of TiNi and Cobalt-Chromium. Unlike the hydrophilic polymer coating on endovascular metallic devices that is currently used, this hydrophilic conversion by UV irradiation does not come off easily. The UV irradiation method helps to reduce the friction of endovascular metallic devices such as those made of titanium containing metal including NiTi or Cobalt-Chromium.

The above data also show that the affinity of a metallic surface (NiTi) with vascular tissue increases after the hydrophilic conversion by UV irradiation. The increase in albumin absorption, endothelial cell attractiveness, and bioactivities of endothelial cells indicates that the biocompatibility of the endovascular metallic device made of NiTi is enhanced by the UV irradiation. The above data indicate that UV treated NiTi devices are covered with more regenerative endothelial cells more quickly than those without UV treatment. The increased affinity and biocompatibility works positively for anti-clot formation on the metallic devices, and helps to achieve a prompt healing of vascular tissue where the metallic devices are placed.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. A prohealing endovascular device, comprising a surface generated by a method comprising:
 irradiating a surface of the endovascular device with a high energy radiation for a period of time to cause the surface to become a super hydrophilic surface.

2. The endovascular device of claim 1, wherein the high energy radiation is ultraviolet.

3. The endovascular device of claim 1, which comprises a metal selected from gold, titanium, platinum, tantalum, niobium, nickel, iron, chromium, cobalt, zirconium, magnesium, magnesium, aluminum, palladium, Nitinol, cobalt-chromium alloy, an alloy formed thereof, or combinations thereof.

4. The endovascular device of claim 1, having an increased rate of endothelialization as compared with an endovascular device without treatment by irradiation.

5. The endovascular device of claim 1, having an increased rate of neointima coverage as compared with an endovascular device without treatment by irradiation.

6. The endovascular device of claim 1, having an increased affinity of the device with a native vascular tissue as compared with an endovascular device without treatment by irradiation.

7. The endovascular device of claim 1, having a reduced friction during the insertion or delivery of the endovascular device.

8. The endovascular device of claim 1, having a decreased level of inflammation response at a site receiving the endovascular device as compared with an endovascular device without treatment by irradiation.

9. The endovascular device of claim 4, wherein the rate of endothelialization is increased by at least 10%.

10. The endovascular device of claim 5, wherein the rate of neointima coverage is increased by at least 10%.

11. The endovascular device of claim 6, wherein the affinity is increased by at least 10%.

12. The endovascular device of claim 7, wherein the friction is decreased by at least 10%.

13. The endovascular device of claim 8, wherein the level of inflammation response is decreased by at least 10%.

14. The endovascular device of claim 1, wherein the method further comprises surface-treating the endovascular device prior to irradiating the surface of the endovascular device.

15. The endovascular device of claim 1, which is selected from stents, grafts, stent-grafts, catheters, leads and electrodes, clips, shunts, closure devices, valves, guidewires, filters, cage-like vascular plug, coils, and particles.

16. A method of treating or ameliorating a disorder involving a vascular condition, comprising implanting in a subject the endovascular device of claim 1.

17. The method of claim 16, wherein the disorder is selected from the group consisting of atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, urethral obstruction and tumor obstruction.

18. A method of generating an endovascular device according to claim 1, comprising:
 irradiating a surface of the endovascular device with a high energy radiation for a period of time to cause the surface to become a super hydrophilic surface, thereby generating the endovascular device.

19. The method of claim 18, further comprising surface-treating the endovascular device prior to irradiating the surface of the endovascular device.

20. The method of claim 17, wherein surface-treating comprises treating the endovascular device by acid-etching, sandblasting, or machining.

21. The method of claim 18, wherein the period is about 10 minutes or longer.

* * * * *